US007585621B2

(12) United States Patent
Beall et al.

(10) Patent No.: US 7,585,621 B2
(45) Date of Patent: Sep. 8, 2009

(54) DETECTION OF WEST NILE VIRUS INFECTION AND VACCINATION

(75) Inventors: Melissa Beall, Cape Elizabeth, ME (US); Ramaswamy Chandrashekar, Scarborough, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 66 days.

(21) Appl. No.: 10/937,157

(22) Filed: Sep. 9, 2004

(65) Prior Publication Data
US 2005/0053923 A1 Mar. 10, 2005

Related U.S. Application Data

(60) Provisional application No. 60/501,390, filed on Sep. 9, 2003.

(51) Int. Cl.
*C12Q 1/70* (2006.01)
*A61K 39/12* (2006.01)
(52) U.S. Cl. .......................................... 435/5; 424/218.1
(58) Field of Classification Search ..................... 435/6, 435/5, 345; 424/159.1, 199.1
See application file for complete search history.

(56) References Cited

U.S. PATENT DOCUMENTS

| 5,122,447 | A | * | 6/1992 | McGinley et al. | .............. | 435/5 |
| 5,736,319 | A | * | 4/1998 | Cochran | ....................... | 435/5 |
| 6,156,499 | A | * | 12/2000 | Stewart et al. | ................. | 435/5 |
| 2003/0022849 | A1 | | 1/2003 | Chang | | |
| 2003/0091595 | A1 | | 5/2003 | Chu | | |
| 2003/0104008 | A1 | * | 6/2003 | Loosmore et al. | ........ | 424/204.1 |
| 2003/0148261 | A1 | | 8/2003 | Fikrig et al. | | |
| 2003/0149252 | A1 | | 8/2003 | Gourdin et al. | | |
| 2004/0037848 | A1 | | 2/2004 | Audonnet et al. | | |
| 2004/0197769 | A1 | | 10/2004 | Wong et al. | | |

FOREIGN PATENT DOCUMENTS

| WO | 0075665 | 12/2000 |
| WO | 02 072036 | 9/2002 |
| WO | 02 081754 | 10/2002 |
| WO | 04 040263 | 5/2004 |
| WO | 0440263 | 5/2004 |
| WO | 0524427 | 3/2005 |

OTHER PUBLICATIONS

Martens et al (Journal of Swine Health and Production 11 (2): 81-85, published Mar./Apr. 2003.*
van Oirschot et al (Journal of Virological Methods 67:23-34, 1997).*
Ahmad et al (Virology 192:207-216, 1993).*
Lanciotti et al (Science 286:2333-2337, 1999) (in IDS).*
Ebel, G., et al., *Detection by Enzyme-Linked Immunosorbent Assay of Antibodies to West Nile Virus in Birds*, Emerging Infectious Diseases 8(9):979-981 (2002).

Martin, D., et al., *Standarization of Immunoglobulin M Capture Enzyme-Linked Immunosorbent Assays for Routine Diagnosis of Arboviral Infections*, Journal of Clinical Microbiology 38(5):1823-1826 (2000).
Martin, D., et al., *Use of Immunoglobulin M Cross-Reactions in Differential Diagnosis of Human Flaviviral Encephalitis Infections in the United States*, Clinical and Diagnostic Laboratory Immunology 9(3):544-549 (2002).
Cantile, C., et al., *Clinical and neuropathological features of West Nile Virusequine encephalomyelitis in Italy*, Equine Vet. J, 32(1):31-35 (2000).
Feinstein, S., et al., *Determination of Human IgG and IgM Class Antibodies to West Nile Virus by Enzyme Linked Immunosorbent Assay (ELISA)*, J. Med. Virol. 17(1):63-72 (1985).
Lanciotti, R., et al., *Origin of the West Nile Virus Responsible for an Outbreak of Encephalitis in the Northeastern United States*, Science 286 (17):2333-2337 (1999).
Hall, R., et al., *Epitope Analysis of the Envelope and Non-Structural Glycoproteins of Murray Valley Encephalitis Virus*, Journal of General Virology 71:2923-2930 (1990).
Hall, R., et a.l, *Monoclonal Antibodies to Kunjin and Kokobera Viruses*, Immunology and Cell Biology 69:47-49 (1991).
Hall, R., et a.l, *Immunodominant Epitopes on the NS1 Protein of MVE and KUN Viruses serve as targets for a blocking ELISA to Detect Virus-Specific Antibodies in Sentinel Animal Serum*, Journal of Virological Methods 51:201-210 (1995).
Blitvich, et al., *Serologic Evidence of West Nile Virus Infection in Horses*, Coahuila State, Mexico, Emerging Infectious Diseases 9(7):853-856 (2003).
Blitvich, et al., *Epitope-Blocking Enzyme-Linked Immunosorbent Assays for the Detection of Serum Antibodies to West Nile Virus in Multiple Avian Species*, Journal of Clinical Microbiology 41(3):1041-1047 (2003).
Yamshchikov, et al., *An Infectious Clone of the West Nile Flavivirus*, Virology 281:294-304(2001).
Hubálek, et al., *West Nile Fever—a Reemerging Mosquito-Borne Viral Disease in Europe*, Emerging Infectious Diseases 5:643-650 (1999).
Shi, Pei-Yong, et al., "Serologic Diagnosis of West Nile Virus Infection", Expert Review of Molecular Diagnostics, 2003, vol. 3(6), pp. 733-741.

(Continued)

*Primary Examiner*—Mary E Mosher
(74) *Attorney, Agent, or Firm*—McDonnell Boehnen Hulbert & Berghoff LLP

(57) ABSTRACT

A method and device for determining whether an animal is infected with West Nile Virus (WNV), or is either not infected or vaccinated with a WNV vaccine. The method includes contacting a biological sample from the subject with a first WNV polypeptide that is not an element of the WNV vaccine, and detecting whether antibodies in the sample bind to the WNV polypeptide. If the antibodies in the sample bind to the WNV polypeptide, it can be determined that the animal is naturally infected with WNV and if the antibodies do not bind to the polypeptide, it can be determined that the animal is either vaccinated or not infected.

8 Claims, 2 Drawing Sheets

OTHER PUBLICATIONS

Davis, B., et al. "*West Nile Virus Recombinant DNA Vaccine Protects Mouse and Horse from Virus Challenge and Expresses In Vitro a Noninfectious Recombinant Antigen that can be Used in Enzyme-Linked Immunosorbent Assays*", Journal of Virology, 2001, vol. 75(9), pp. 4040-4047.

Wong, Susan, et al., "*Immunoassay Targeting Nonstructural Protein 5 to Differentiate West Nile Virus Infection from Dengue and St. Louis Encephalitis Virus Infections and from Flavivirus Vaccination*", Journal of Clinical Microbiology, 2003, vol. 41(9), pp. 4217-4223.

Porter, Michael B., et al., "*Immunoglobulin M-Capture Enzyme-Linked Immunosorbent Assay Testing of Cerebrospinal Fluid and Serum from Horses Exposed to West Nile Virus by Vaccination or Natural Infection*", J. Vet. Intern Med., 2004, vol. 18, pp. 866-870.

Wong, Susan J., et al., *Immunoassay Targeting Nonstructural Protein 5 to Differentiate West Nile Virus Infection from Dengue and St. Louis Encephalitis Virus Infections and from Flavivirus Vaccination*, Journal of Clinical Microbiology 41(9):4217-4223 (2003).

Jozan, Martine, et al., *Detection of West Nile Virus Infection in Birds in the United States by Blocking ELISA and Immunohistochemistry*, Vector-Borne and Zoonotic Diseases 3(3):99-110 (2003).

Beasley DW, et al.,*Identification of neutralizing epitopes within structural domain III of he West Nile virus envelope protein*, J. Virol. 76(24):13097-13100 (2002).

Davis, B.S., et al., *West Nile virus recombinant DNA vaccine protects mouse and horse from virus challenge and expresses in vitro a non-infectious recombinant antigen that can be used in enzyme-linked immunosorbent assays*, J. Virol. 75(9):4040-4047 (2001).

Seppanen, H., *Development of a highly specific and sensitive rubella immunoglobulin M. antibody capture enzyme immunoassay that uses enzyme-labeled antigen*, Journal of Clinical Microbiology 28(4):719-723 (1990).

Wang, T, et al., *Immunization of mice against West Nile Virus with recombinant envelope protein*, J Immunol. 167(9):5273-5277 (2001).

Wang, T., et al., *West Nile virus envelope protein: role in diagnosis and immunity*, Ann NY Acad Sci. 951:325-327 (2001).

Wang, T., et al., *A recombinant envelope protein-based enzyme-linked immunosorbent assay for West Nile virus serodiagnosis*, Vector Borne Zoonotic Dis. 2(2):105-109 (2002).

Wong, S.J., et al., *Detection of human anti-flavivirus antibodies with a west nile virus recombinant antigen microsphere immunoassay*, J. Clin Microbiol. 42(1):65-72 (2004).

* cited by examiner

FIG. 1

MAFLVNVALVFMVVYISYIYAIMAISTGCAINISRQELRCGSGVFIHNDVEAWMDRYKY

YPETPQGLAKIIQKAHKEGVCGLRSVSRLEHQMWEAVKDELNTLLKENGVDLSVVVEKQ

EGMYKSAPKRLTATTEKLEIGWKAWGKSILFAPELANNTFVVDGPETKECPTQNRAWNS

LEVEDFGFGLTSTRMFLKVRESNTTECDSKIIGTAVKNNLAIHSDLSYWIESRLNDTWK

LERAVLGEVKSCTWPETHTLWGDGILESDLIIPVTLAGPRSNHNRRPGYKTQNQGPWDE

GRVEIDFDYCPGTTVTLSESCGHRGPATRTTTESGKLITDWCCRSCTLPPLRYQTDSGC

WYGMEIRPQRHDEKTLVQSQVNAYLEHHHHHHHH    [SEQ ID NO: 1]

FIG. 2

ISTGCAINISRQELRCGSGVFIHNDVEAWMDRYKYYPETPQGLAKIIQKAHKEGVCGLR

SVSRLEHQMWEAVKDELNTLLKENGVDLSVVVEKQEGMYKSAPKRLTATTEKLEIGWKA

WGKSILFAPELANNTFVVDGPETKECPTQNRAWNSLEVEDFGFGLTSTRMFLKVRESNT

TECDSKIIGTAVKNNLAIHSDLSYWIESRLNDTWKLERAVLGEVKSCTWPETHTLWGDG

ILESDLIIPVTLAGPRSNHNRRPGYKTQNQGPWDEGRVEIDFDYCPGTTVTLSESCGHR

GPATRTTTESGKLITDWCCRSCTLPPLRYQTDSGCWYGMEIRPQRHDEKTLVQSQVNAY

LEHHHHHHHH    [SEQ ID NO: 2]

FIG. 3

MDRSIALTFLAVGGVLLFLSVNVHADTGCAIDISRQELRCGSGVFIHNDVEAWMDRYKY
YPETPQGLAKIIQKAHKEGVCGLRSVSRLEHQMWEAVKDELNTLLKENGVDLSVVVEKQ
EGMYKSAPKRLTATTEKLEIGWKAWGKSILFAPELANNTFVVDGPETKECPTQNRAWNS
LEVEDFGFGLTSTRMFLKVRESNTTECDSKIIGTAVKNNLAIHSDLSYWIESRLNDTWK
LERAVLGEVKSCTWPETHTLWGDGILESDLIIPVTLAGPRSNHNRRPGYKTQNQGPWDE
GRVEIDFDYCPGTTVTLSESCGHRGPATRTTTESGKLITDWCCRSCTLPPLRYQTDSGC
WYGMEIRPQRHDEKTLVQSQVNA

[SEQ ID NO: 3]

FIG. 4

DTGCAIDISRQELRCGSGVFIHNDVEAWMDRYKYYPETPQGLAKIIQKAHKEGVCGLRS
VSRLEHQMWEAVKDELNTLLKENGVDLSVVVEKQEGMYKSAPKRLTATTEKLEIGWKAW
GKSILFAPELANNTFVVDGPETKECPTQNRAWNSLEVEDFGFGLTSTRMFLKVRESNTT
ECDSKIIGTAVKNNLAIHSDLSYWIESRLNDTWKLERAVLGEVKSCTWPETHTLWGDGI
LESDLIIPVTLAGPRSNHNRRPGYKTQNQGPWDEGRVEIDFDYCPGTTVTLSESCGHRG
PATRTTTESGKLITDWCCRSCTLPPLRYQTDSGCWYGMEIRPQRHDEKTLVQSQVNA

[SEQ ID NO: 4]

DETECTION OF WEST NILE VIRUS INFECTION AND VACCINATION

BACKGROUND OF THE INVENTION

1. Field of the Invention

The invention is related to the detection of West Nile Virus (WNV) infections in animals. More specifically, the invention is related to a method for distinguishing animals that have been infected with WNV from animals that have been vaccinated against WNV or have not been infected with WNV.

2. Description of Related Art

Known as a Flavivirus, the West Nile virus was first identified in 1937 in Africa and first found in North America in 1999. Migratory birds are considered the primary means whereby infection is spread within and between countries. The virus is transmitted by mosquitoes that have acquired infection by feeding on viremic birds. The virus is then amplified during periods of adult mosquito blood-feeding. Infected mosquitoes then transmit the virus to humans and animals upon feeding thereon.

West Nile virus is the causative agent for West Nile Virus disease, particularly West Nile encephalitis, predominately in humans, other mammals and birds. The chief concern in both the United States and foreign countries is the lack of effective treatment for West Nile virus disease. Anti-inflammatory drugs are used to combat swelling of central nervous system tissues, but beyond that no medical intervention is currently available.

The West Nile fever virus also affects horses, particularly in North America and Europe (Cantile C. et al., Equine Vet. J., 2000, 32 (1), 31-35). These horses reveal signs of ataxia, weakness of the rear limbs, paresis evolving towards tetraplegia and death. Horses and camels are the main animals manifesting clinical signs in the form of encephalitis.

The virions of the West Nile fever virus are spherical particles with a diameter of 50 nm constituted by a lipoproteic envelope surrounding an icosahedric nucleocapsid containing a positive polarity, single-strand RNA. A single open reading frame (ORF) encodes all the viral proteins in the form of a polyprotein. The cleaving and maturation of this polyprotein leads to the production of several different viral proteins. The structural proteins are encoded by the 5' part of the genome and correspond to the nucleocapsid designated C (14 kDa), the envelope glycoprotein designated E (50 kDa), the pre-membrane protein designated prM (23 kDa), and the membrane protein designated M (7 kDa). The non-structural proteins are encoded by the 3' part of the genome and correspond to the proteins NS1 (40 kDa), NS2A (19 kDa), NS2B (14 kDa), NS3 (74 kDa), NS4A (15 kDa), NS4B (29 kDa), and NS5 (97 kDa).

Vaccines for WNV are described, for example, in U.S. Patent Publication Nos. 2003/0148261A1, 2003/0104008A1 and 2003/0091595A1, each of which is incorporated herein by reference in its entirety. Publication No. 2003/0091595 describes a WNV vaccine that includes an inactivated whole or subunit WNV. Publication No. 2003/0104008 discloses a vector, such as recombinant avipox virus, containing and expressing exogenous polynucleotide(s) from WNV to induce an immune response against WNV. These recombinant WNV vaccines include a vector containing a polynucleotide having single encoding frame corresponding to, for example, prM-E, M-E and prM-M-E. The vector may include several separate polynucleotides encoding the different proteins (e.g. prM and/or M and E). The vector can also include polynucleotides corresponding to more than one WN virus strain, for example, two or more polynucleotides encoding E or prM-M-E of different strains. Furthermore, the vector can include one or more nucleotide sequences encoding immunogens of other pathogenic agents and/or cytokines. Publication No. 2003/0148261 describes various WNV polypeptides and immunogenic fragments for use in WNV vaccines. These vaccines are produced recombinantly using various vectors encoding WNV polypeptides and the vectors are expressed by a variety of host cells.

SUMMARY OF THE INVENTION

In one aspect, the invention provides a method for determining whether an animal is infected with West Nile Virus (WNV), or is either not infected or is vaccinated with a WNV vaccine. The method includes contacting a biological sample from the animal with a first WNV polypeptide that is not an element of the WNV vaccine and detecting whether an antibody in the sample binds to the first WNV polypeptide. If an antibody in the sample binds to the WNV polypeptide, the animal is naturally infected with WNV and if an antibody does not bind to the polypeptide, the animal is either vaccinated or is not infected. The method also includes detecting, in a sample that does not have an antibody that binds to the first WNV polypeptide, whether an antibody in the sample binds to a second WNV polypeptide that is an element of a WNV vaccine, and determining that the animal has been vaccinated by detecting that an antibody in the sample binds to the second WNV polypeptide.

In another aspect, the invention provides for a method of distinguishing between animals that have been naturally infected with WNV and animals that have not been infected or have been vaccinated with a WNV vaccine. The method includes contacting a biological sample from an animal with a first WNV polypeptide that does not substantially bind to antibodies that are a significant component of the animal's immune response to the WNV vaccine, detecting whether the antibody in the sample binds to the first WNV polypeptide, and determining that the animal is naturally infected by correlating a positive result in the detecting step to a natural infection and determining that the animal has been vaccinated or is not infected by correlating a negative result to a vaccination or no infection. In those samples that do not have an antibody that substantially binds to the first WNV polypeptide, the method may further include detecting whether an antibody in the sample binds to a second WNV polypeptide that substantially binds an antibody that is a significant component of the animal's immune response to the vaccine, thereby determining whether the animal has been vaccinated.

In a further aspect, the invention is directed to a method of determining whether an animal is either not infected or has been vaccinated against WNV with a WNV vaccine, or is naturally infected with WNV. The method includes determining the animal's immune response to a first polypeptide derived from WNV that is not an element of a WNV vaccine. In those animal that do not have an immune response to the first polypeptide, the method may further include determining whether the animal has been vaccinated by determining the animal's immune response to a second polypeptide that is an element of the WNV vaccine.

In yet another aspect, the invention is directed to a method for determining the vaccination or infection status of an animal for WNV. The method includes contacting a biological sample from the animal with a reagent comprising a first WNV polypeptide that is not an element of a WNV vaccine, and detecting whether the first WNV polypeptide binds to an antibody in the biological sample. If the polypeptide binds to an antibody in the sample, the animal is infected and wherein, if the polypeptide does not bind to an antibody in the sample, the animal is either not infected or has been vaccinated with a vaccine that does not comprise the first WNV polypeptide. In those samples that do not have an antibody that substantially binds to the first WNV polypeptide, the method may further include detecting whether an antibody in the sample binds to a second WNV polypeptide that substantially binds an antibody that is a significant component of the animal's immune response to the vaccine, thereby determining whether the animal has been vaccinated.

Still further, the invention provides a method of determining whether an animal is infected with West Nile Virus (WNV), is vaccinated with a WNV vaccine, or is not infected and not vaccinated. The method includes contacting a biological sample from the animal with a first WNV polypeptide that is not an element of the WNV vaccine, contacting the biological sample with a second WNV polypeptide that is an element of the WNV vaccine, and detecting whether antibodies in the sample bind to the first and the second WNV polypeptides. If antibodies in the sample bind to both the first and second WNV polypeptides, the animal is naturally infected with WNV. If an antibody in the sample binds to the second WNV polypeptide but not the first WNV polypeptide, the animal has been vaccinated but is not naturally infected. If an antibody does not bind to the either polypeptide, the animal is not infected and not vaccinated.

The invention also provides for a method of determining an animal's vaccination and infection status for WNV. The method includes contacting a biological sample from an animal with a first polypeptide that does not substantially bind to antibodies that are a significant component of the animal's immune response to a WNV vaccine and a second polypeptide that substantially binds to an antibody that is a significant component of the animal's immune response to a WNV vaccine, detecting whether antibodies in the sample bind to the first and second polypeptides, and determining that the animal is naturally infected by detecting the binding of antibodies in the sample to both the first and second polypeptides, determining that that the animal is vaccinated and not infected by detecting the binding of an antibody to the second polypeptide but not the first polypeptide, and determining that the animal is not vaccinated and not infected by detecting the absence of binding to the first and second WNV polypeptides.

In the various aspects of the invention, the first WNV polypeptide may be a WNV NS1 polypeptide. The second WNV polypeptide may be a polypeptide selected from E, prM, M-E and prM-M-E. The WNV vaccine may include at least one WNV polypeptide selected from prM, M-E, prM-M-E and E. The WNV vaccine may be a vector encoding at least one polypeptide selected from prM, M-E, prM-M-E and E.

BRIEF DESCRIPTION OF THE FIGURES

FIG. 1 is the polypeptide sequence [SEQ ID NO:1] of the expression product of a vector containing the secretory signal sequence for honey bee melittin (GenBank P01501) upstream of the West Nile virus NS1 sequence in the pTRIEX1.1 Neo vector (Invitrogen) in frame with an 8-His tag. The underlined portion is the signal sequence that is cleaved to provide the mature protein.

FIG. 2. is the polypeptide sequence shown FIG. 1 without the signal sequence [SEQ ID NO:2].

FIG. 3 is the polypeptide sequence [SEQ ID NO:3] of the expression product of a vector containing the native secretory signal sequence from the 3'end of the West Nile virus E protein in frame with the NS1 sequence in the pcDNA3.2/ GW/D-TOPO vector (Invitrogen) in frame with a V5 tag. The underlined portion is the signal sequence that is cleaved to provide the mature protein.

FIG. 4 is the polypeptide sequence of FIG. 3 without the signal sequence [SEQ ID NO:4].

DETAILED DESCRIPTION

Before describing the present invention in detail, a number of terms will be defined. As used herein, the singular forms "a," "an", and "the" include plural referents unless the context clearly dictates otherwise.

As used herein, the term "polypeptide" refers to a compound of a single chain or a complex of two or more chains of amino acid residues linked by peptide bonds. The chain(s) may be of any length and may consist of a fusion protein. Although "protein" is often used in reference to relatively large polypeptides, and "peptide" is often used in reference to small polypeptides, usage of these terms in the art overlaps and varies. The term "polypeptide" as used herein thus refers interchangeably to peptides, polypeptides, or fusion proteins unless otherwise noted. The term "amino acid" refers to a monomeric unit of a peptide, polypeptide or protein.

As used herein, a "derivative" of a WNV polypeptide, or a polypeptide that is "derived from" a WNV polypeptide, refers to a polypeptide in which the native form has been purified, modified or altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which may result in changes in primary, secondary or tertiary structure.

"Binding specificity" or "specific binding" refers to the substantial recognition of a first molecule for a second molecule, for example a polypeptide and a polyclonal or monoclonal antibody, or an antibody fragment (e.g. a Fv, single chain Fv, Fab', or F(ab')2 fragment) specific for the polypeptide.

"Substantial binding" or "substantially bind" refer to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and incubation time and temperature. In another aspect, one molecule is substantially incapable of binding or recognizing another molecule in a cross-reactivity sense where the first molecule exhibits a reactivity for a second molecule that is less than 25%, preferably less than 10%, more preferably less than 5% of the reactivity exhibited toward a third molecule under a particular set of assay conditions, which includes the relative concentration, and incubation time and temperature. Specific binding can be tested using a number of widely known methods, e.g, an immunohistochemical assay, an enzyme-linked immunosorbent assay (ELISA), a radioimmunoassay (RIA), or a western blot assay.

A "biological sample" is any sample from an animal that is expected to contain immunoglobulins. Generally, these samples are whole blood and blood components, but in some circumstances may include saliva, urine, tears, other bodily fluids, tissue extracts or cellular extracts.

An "infection," such as in a WNV infection, means that an animal has been exposed to WNV, regardless of whether the animal exhibits clinical symptoms of WNV. A natural infection refers to an exposure that occurs as a result of one of the natural transmission methods for WNV, such as a mosquito bite. An infection does not include an exposure to WNV through vaccination.

A "polypeptide that is not an element of a WNV vaccine" is any WNV polypeptide that is not present in, or is not an immunogenically active portion of, a WNV vaccine. For example, when an animal is vaccinated with a vaccine using one or more of the prM, M or E polypeptides, but does not contain an NS1 polypeptide, the NS1 polypeptide is a polypeptide that is not an element of the vaccine. Elements of the vaccine can be portions of a subunit vaccine that includes less than the entire virus; these portions can be chemically synthesized or expressed recombinantly before becoming part of the vaccine, and these portions can be encoded by one or more vectors that express an the immunogenic composition in vivo.

An "antibody that is a significant component of an animal's immune response to a WNV vaccine" refers to an antibody that is elicited as the result of a vaccination with a WNV vaccine. These antibodies may be identical to or similar to antibodies elicited as the result of a natural WNV infection. These antibodies will be maintained at a sufficient titer and so as to provide a protective and neutralizing effect against the virus. A successful vaccination produces a measurable level of the antibody that is a significant component of the WNV vaccine.

Biological samples from animals that have been vaccinated against a WNV infection have the potential for producing a positive result in a test for a WNV infection due to the presence of antibodies produced in response to the vaccine. In one aspect, the invention provides for a method of distinguishing between animals that have been naturally infected with WNV from animals that have not been infected or have been vaccinated against a WNV infection. The method includes contacting a biological sample from the animal with a polypeptide derived from WNV that does not substantially bind to an antibody that is a significant component of the animal's antibody response to a WNV vaccine.

In one aspect, the WNV polypeptide is not an element of a WNV vaccine, such as a WNV NS1 polypeptide. FIGS. 2 and 4 are examples of two WNV polypeptides useful in the method of the invention. SEQ ID NO:1 is the product from the expression of the secretory signal sequence for honey bee melittin (GenBank P01501) upstream of the West Nile virus NS1 sequence in the pTRIEX1.1 Neo vector (Invitrogen) in frame with an 8-His tag. The underlined portion of the sequence in FIG. 1 is the signal sequence that is cleaved to provide the mature protein [SEQ ID. NO:2]. SEQ ID NO:3 is the product from the expression of the native secretory signal sequence from the 3'end of the West Nile virus E protein in frame with the NS1 sequence in the pcDNA3.2/GW/D-TOPO vector (Invitrogen) in frame with a V5 tag. The underlined portion of the sequence in FIG. 2 is the signal sequence that is cleaved to provide the mature protein [SEQ ID NO 4].

SEQ ID. NOs: 2 and 4 can be used to detect whether an animal has been vaccinated with a vaccine that does not contain the WNV NS1 polypeptide as an element of the vaccine. The complete sequences are not required and may include only an immunodominant region of the sequences. Such sequences are known as the subunits of the antigenic determinant that are most easily recognized by the immune system and thus most influence the specificity of the induced antibody. The sequences may contain more than one immunodominant regions.

The development of WNV antibodies in an animal against a vaccine is dependent upon the vaccine. The difference in the immune response between animals that are vaccinated and animals that are naturally infected provides a means for determining whether an animal has been vaccinated or is naturally infected. Using the method of the invention, animals that have been naturally infected with WNV can be distinguished from animals that have not been infected or have been vaccinated against a WNV infection. Accordingly, the detection of the binding between a polypeptide derived from WNV and an antibody that is not a significant component of an animal's immune response to a vaccine can indicate a natural infection. The absence of such binding can indicate vaccination or no infection. In addition, a second, separate antibody capture reagent, such as an WNV polypeptide that substantially binds an antibody that is a significant component of animal's immune response to a WNV vaccine, can be included in the test that detects antibodies produced in response to vaccination. The detection of neither antibody indicates no infection and no vaccination. As such, various combinations of separate capture reagents can lead to a determination of the vaccination and/or infection status of the test subject.

In one aspect, the method of the invention includes contacting a biological sample from an animal with a polypeptide that is a part of the native virus but is not an element of WNV vaccine. An animal is any mammal that is likely to be vaccinated against WNV and in particular equines. In addition, humans may ultimately be vaccinated against WNV. In another aspect, the invention includes a method of determining whether an animal has not been infected by WNV and has not been vaccinated against WNV. A biological sample from an animal is analyzed to detect the presence or absence of antibodies against a polypeptide derived from WNV that is not an element of a WNV vaccine. It is then determined that the animal has not been infected and has not been or vaccinated by determining the absence of such antibodies.

In one aspect of the invention, a polypeptide that is not an element of a WNV vaccine is an NS1 polypeptide. When an animal is vaccinated with a WNV including a WNV E polypeptide, WNV E is a polypeptide that is an element of a WNV vaccine. Using WNV NS1 and WNV E polypeptides, the vaccination or infection status of an animal can be determined by detecting whether antibodies in the sample bind to one or both polypeptides. If antibodies in the sample bind to either of the polypeptides, the animal is either vaccinated or infected. If no antibody binds the NS1 polypeptide (i.e. antibodies bind only the E polypeptide), then it can be determined that the animal has been vaccinated. If no binding is detected for either polypeptide, then it can be determined that the animal is not infected and not vaccinated. The analysis is summarized here in Table 1 as a non-limiting example of the determination of the vaccination or infection status of an animal.

TABLE 1

| | Antibodies detected to: | | |
|---|---|---|---|
| | NS1 | E | Status |
| Result 1 | + | + | infected |
| Result 2 | − | + | vaccinated |
| Result 3 | − | − | not infected/not vaccinated |

Antibodies to WNV can be determined from biological fluids or tissues by any method known in the art. The simplest methods generally are immunoassay methods. One such method is a competition based method wherein serum samples are preincubated with an WNV polypeptide that is not an element of a WNV vaccine, and then added to a solid phase, such a microtiter plate, having an immobilized monoclonal antibody against the WNV polypeptide. Antibodies to WNV in the sample will prevent the WNV polypeptide from binding to the immobilized antibody. Detection of the binding of the WNV polypeptide to the immobilized antibody can be determined by adding a second binding partner for the WNV polypeptide, either directly labeled or capable of becoming labeled through binding to another binding partner having a label. In this method, a positive sample, i.e. a sample having WNV antibodies, is associated with a decrease in signal from the label. Thus, for this method, the decrease in signal is a positive result that can be correlated to the presence of a WNV antibody in the sample.

In one particular embodiment, antibodies to WNV NS1 in a biological sample can be detected by contacting the sample with a WNV NS1 polypeptide and adding the sample to microtiter plate coated with an anti-NS1 monoclonal antibody. Binding of NS1 to the microtiter plate can be detected by adding a rabbit polyclonal antibody against WNV NS1 and adding an HRP-conjugated Donkey anti-rabbit polyclonal antibody. Antibodies in the sample will prevent the binding of NS1 to the immobilized antibody, thereby causing a decrease in signal. Therefore, in this embodiment, the decrease in signal is a positive result that can be correlated to the presence of WNV antibody in the sample.

Another method for detecting WNV antibodies is a sandwich assay where a biological sample suspected of containing a WNV is contacted with an immobilized WNV polypeptide to form a immunological complex. The presence of WNV antibody is determined by the detection of the binding of a labeled binding partner for the WNV antibody, such a second antibody. In this method, the detecting of the binding is a positive result that can be correlated to the presence of antibody to WNV in the sample.

In one aspect of the invention, the WNV polypeptides are immobilized on a suitable solid support. The biological sample is brought into contact with the polypeptide, to which the anti-WNV antibodies bind, if such antibodies are present in the sample. The binding may be detected by any suitable means, e.g., enzymes, radionuclides, particulates or fluorescent labels. In a suitable embodiment, the detection reagent can be associated with a protein that is the same or similar to that which is used to capture anti-WNV antibodies (if present). In one particular embodiment, antibodies to WNV E can be detected by immobilizing a WNV E polypeptide on a solid support. Biological samples can be contacted with the solid support and, following the removal of unbound sample, binding of the WNV E antibodies to the WNV polypeptide can be accomplished with a labeled IgG antibody.

The polypeptides used in the invention contain at least six amino acids, usually at least nine amino acids, and more usually twelve or more amino acids found within one of the natural WNV polypeptides and mimitopes and variants thereof. For example, WNV variants within the scope of the invention may comprise conservatively substituted sequences, meaning that one or more amino acid residues of the WNV polypeptide are replaced by different residues that do not alter the secondary and/or tertiary structure of the WNV polypeptide. Such substitutions may include the replacement of an amino acid by a residue having similar physicochemical properties, such as, for purposes of example only, substituting one aliphatic residue (Ile, Val, Leu, or Ala) for another, or substitution of basic residues Lys and Arg, acidic residues Glu and Asp, amide residues Gln and Asn, hydroxyl residues Ser and Tyr, or aromatic residues Phe and Tyr. Further information regarding the making of phenotypically silent amino acid exchanges may be found in Bowie et al., *Science* 247:1306-1310 (1990). Other WNV variants that retain substantially the antigenicity of the WNV polypeptides are also contemplated as well as those where the amino acid substitutions are made in the area outside the antibody recognition regions of the protein. Fusion proteins comprising two or more polypeptide sequences of WNV are also within the scope of the invention provided the sequences provide the appropriate antigenicity. Such polypeptides will generally correspond to at least one epitope or mimitope that is characteristic of WNV. By characteristic, it is meant that the epitope or mimitope will allow immunologic detection of antibody directed to WNV in a physiological sample with reasonable assurance. Usually, it will be desirable that the epitope or mimitope, variant or fusion protein be immunologically distinct from (i.e., not cross-reactive with antibodies which recognize) viruses other than WNV.

The WNV polypeptides used as detection reagents may be natural, i.e., isolated from a natural source, or may be synthetic. The natural proteins may be isolated from the whole virus that is obtained as described above by conventional techniques, such as affinity chromatography. Polyclonal or monoclonal antibodies may be used to prepare a suitable affinity column by well-known techniques.

Proteins that are immunologically cross-reactive with a natural WNV protein can be chemically synthesized. For example, polypeptides having fewer than about 100 amino acids, more usually fewer than about 80 amino acids, and typically fewer than about 50 amino acids, may be synthesized by the well-known Merrifield solid-phase synthesis method where amino acids are sequentially added to a growing chain. Merrifield, 1963, J. Am. Chem. Soc., 85:2149-2156). Recombinant proteins can also be used. These proteins may be produced by expression in cultured cells of recombinant DNA molecules encoding a desired portion of the WNV genome. The portion of the WNV genome may itself be natural or synthetic, with natural genes obtainable from the isolated virus by conventional techniques. Of course, the genome of WNV is RNA, and it will be necessary to transcribe the natural RNA into DNA by conventional techniques employing reverse transcriptase. Polynucleotides may also be synthesized by well-known techniques. For example, short single-stranded DNA fragments may be prepared by the phosphoramidite method described by Beaucage and Carruthers, 1981, Tett. Letters 22:1859-1862. Double-stranded fragments may then be obtained either by synthesizing the complementary strand and then annealing the strands together under appropriate conditions, or by adding the complementary strand using DNA polymerase with an appropriate primer sequence.

The natural or synthetic DNA fragments coding for the desired WNV protein or fragment may be incorporated in a DNA construct capable of introduction to and expression in in vitro cell culture. Usually, the DNA constructs will be suitable for replication in a unicellular host, such as yeast or bacteria. They may also be intended for introduction and integration within the genome of cultured mammalian or other eukaryotic cells. DNA constructs prepared for introduction into bacteria or yeast will include a replication system recognized by the host, the WNV DNA fragment encoding the desired polypeptide product, transcriptional and translational initiation regulatory sequences joined to the 5'-end of the WNV DNA termination regulatory sequences joined to the 3'-end of the fragment. The transcriptional regulatory sequences will include a heterologus promoter that is recognized by the host. Conveniently, a variety of suitable expression vectors are commercially available for a number of hosts. The complete nucleotide sequence for WNV is available from GenBank as accession number AF196835.

To be useful in the detection methods of the present invention, the polypeptides are obtained in a substantially pure form, that is, typically from about 50% w/w or more purity, substantially free of interfering proteins and contaminants. Preferably, the WNV polypeptides are isolated or synthesized in a purity of at least 80% w/w, and more preferably, in at least about 95% w/w purity. Using conventional protein purification techniques, homogeneous polypeptide compositions of at least about 99% w/w purity can be obtained. For example, the proteins may be purified by use of the antibodies described hereinafter using the immunoabsorbant affinity columns described hereinabove.

The method of the invention may be accomplished using immunoassay techniques well known to those of skill in the art, including, but not limited to, using microplates and lateral flow devices. In one embodiment, one or more WNV polypeptides are immobilized on a solid support at a distinct location. Detection of polypeptide-antibody complexes on the solid support can be by any means known in the art. For example, U.S. Pat. No. 5,726,010, which is incorporated herein by reference in its entirety, describes an example of a lateral flow device useful in the present invention. The device of the invention can be used to detect one or more antibodies to WNV polypeptides.

Immobilization of one or more analyte capture reagents, e.g., WNV polypeptides, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules.

Another embodiment of the invention provides a device that is suitable for a lateral flow assay. For example, a test sample is added to a flow matrix at a first region (a sample application zone). The test sample is carried in a fluid flow path by capillary action to a second region of the flow matrix where a label capable of binding and forming a first complex with an analyte in the test sample. The first complex is carried to a third region of the flow matrix where a WNV protein is immobilized at a distinct location. A second complex is formed between an immobilized polypeptide and the first complex including the antibody from the sample. For example, a first complex comprising a gold sol particle and a WNV protein bound to a WNV antibody will specifically bind and form a second complex with a second immobilized WNV protein or with a second antibody directed to WNV antibodies. The label that is part of the second complex can be directly visualized.

In another aspect, the invention includes one or more labeled specific binding reagents that can be mixed with a test sample prior to application to a device of the invention. In this case it is not necessary to have labeled specific binding reagents deposited and dried on a specific binding reagent pad in the device. A labeled specific binding reagent, whether added to a test sample or pre-deposited on the device, can be for example, a labeled antibody that specifically binds an antibody for WNV.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

A WNV polypeptide, e.g., a WNV NS1 polypeptide, can be an immobilized analyte capture reagent in a reaction zone (solid phase). A second analyte capture reagent, i.e. an anti-IgG or anti-IgM antibody, that has been conjugated to a label, can either be added to the sample before the sample is added to the device, or the second analyte capture reagent can be incorporated into the device. For example the labeled specific binding reagent can be deposited and dried on a fluid flow path that provides fluid communication between the sample application zone and the solid phase. Contact of the labeled specific binding reagent with the fluid sample results in dissolution of the labeled specific binging reagent.

The device may also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

The following are provided for exemplification purposes only and are not intended to limit the scope of the invention described in broad terms above. All references cited in this disclosure are incorporated herein by reference.

EXAMPLES

Example 1

Preparation of Recombinant NS1

Two different constructs were used to obtain recombinant NS1 from COS1 cells. The first construct, obtained from Cornell University (Ithaca, N.Y.), contains the secretory signal sequence for honey bee melittin (GenBank P01501) upstream of the West Nile virus NS1 sequence in the pTRIEX1.1 Neo vector (Invitrogen) in frame with the 8-His tag. The translated product from the expression of this construct is SEQ ID NO: 1. The second construct contains the native secretory signal sequence from the 3'end of the West Nile virus E protein in frame with the NS1 sequence in the pcDNA3.2/GW/D-TOPO vector (Invitrogen) in frame with the V5 tag. The translated product from the expression of this construct is SEQ ID NO: 3. For expression, COS1 cells were transiently transfected with each construct using Lipofectamine 2000 (Invitrogen) according to the manufacturers instructions. Supernatants were harvested at 48 hours post-transfection and tested in a sandwich ELISA as in Example 2. Recombinant NS1 containing the His tag was semi-purified using Ni affinity chromatography according to the manufacturers instructions (Invitrogen). The harvested products did not contain the signal sequences.

Example 2

Sandwich ELISA for Recombinant NS1

Immulon 1B 96 well microtiter plates (Dynatech Laboratories) were coated overnight at 4° C. with 10 μg/ml of a monoclonal antibody against Kunjin NS1 (3.1112G, Chemicon International, Temecula, Calif.) in PBS. The plate was then blocked in 3% BSA in Tris buffer (pH 7.5) for two hours at room temperature. Following four washes in PBS/Tween-20, recombinant NS1, diluted 1:5 for the supernatant or 1:25 for the semi-purified protein in Tris buffer diluent (pH 7.5) (available from IDEXX Laboratories, Inc.) was added to the wells and allowed to incubate for 2 hours at room temperature. Following four washes in PBS/Tween-20, a rabbit polyclonal antibody against WNV-NS1 (Cornell University, Ithaca, N.Y.) was added to the wells at a dilution of 1:500 and incubated at room temperature for an hour. Following four washes in PBS/Tween-20, a donkey anti-rabbit HRP conjugated antibody (Jackson ImmunoResearch, West Grove, Pa.) was added to the wells at a dilution of 1:2500 and incubated for an hour at room temperature. Visualization of the substrate was performed using TMB (KPL) and stopped with 1N HCl. The optical densities of individual wells were measured on a microtiter plate reader at a wavelength of 450 nm. The results are shown in Table 2.

TABLE 2

Detection of recombinant NS1 in a sandwich ELISA.

| Sample | O.D. |
|---|---|
| Negative Supernatant (1:5) | 0.101 |
| rNS1 Supernatant (1:5) | 0.577 |
| Semi-purified rNS1 (1:25) | 0.887 |

Example 3

NS1 Competition ELISA for the Detection of Equine Antibodies to NS1

Nine WNV negative and six WNV positive equine serum samples, as determined by antibody ELISA (IgM) and serum neutralizing titers, were obtained from Cornell University. Serum samples were tested in the NS1 sandwich ELISA by pre-incubating a 1:2 dilution of the serum with the rNS1, either as a semi-purified protein or as culture supernatant, for 15 minutes before adding the sample to a microtiter plate prepared as in Example 2. The presence of anti-NS1 antibodies in the equine serum sample prevents the rNS1 from binding to the monoclonal antibody against NS1 that is coated on the plate. This binding can be detected as in Example 2. Hence, a positive sample is associated with a decrease in optical density for that well. Results are expressed as percent inhibition of rNS1 binding based on the control values (((average negative O.D.—test O.D.)/negative O.D.)*100). The cut-off value for the assay was determined by subtracting three standard deviations from the average of the negative samples and entering this value in the previous equation. Inhibition of rNS1 binding of thirty percent or greater is considered positive for WNV (Blitvitch et al., Journal of Clinical Microbiology, 41:1041-47, 2003). Results are displayed in Table 3. All infected horses tested positive for WNV on the ELISA, while none of the uninfected horses showed significant inhibition. These results demonstrate the utility of this test to diagnose WNV infection.

TABLE 3

NS1 competition ELISA for the diagnosis of WNV infection in horses.

| Sample | Status[1] | NS1 ELISA (O.D.)[2] | Inhibition (%)[2] |
|---|---|---|---|
| CU1 | Neg | 0.507 | 12.6 |
| CU2 | Neg | 0.647 | −11.6 |
| CU3 | Neg | 0.671 | −15.7 |
| CU4 | Neg | 0.58 | 0.0 |
| CU5 | Neg | 0.573 | 1.2 |
| CU6 | Neg | 0.614 | −5.9 |
| CU7 | Neg | 0.577 | 0.5 |
| CU9 | Neg | 0.544 | 6.2 |
| CU10 | Neg | 0.602 | −3.8 |
| CU11 | Pos | 0.07 | 87.9 |
| CU12 | Pos | 0.07 | 87.9 |
| CU15 | Pos | 0.068 | 88.3 |
| CU16 | Pos | 0.073 | 87.4 |
| CU18 | Pos | 0.065 | 88.8 |
| CU19 | Pos | 0.069 | 88.1 |

[1]ELISA (IgM) and serum neutralizing titers
[2]Cut-off: O.D. = 0.411 and 29.2% inhibition

Example 4

Seroconversion following vaccination complicates the diagnosis of WNV in the horse, making it difficult to differentiate vaccination from infection. One commercial vaccine approved for use in the horse contains formalin-inactivated West Nile virus obtained from Vero cells (Fort Dodge Animal Health). To test the effects of this vaccine on the NS1 ELISA, blood samples were obtained from thirty naïve horses (Silver Valley Veterinary Clinic, Pinehurst, Id.) pre-vaccination (day 0) and two weeks after the second in a series of two vaccinations (day 35). Serum samples were assayed using the NS1 assay as in Example 3. Results are shown in Table 4. Twentysix of thirty horses demonstrate inhibition of 30% or greater indicating antibodies to NS1 two weeks following the vaccination protocol.

TABLE 4

Detection of antibodies to NS1 in naive horses vaccinated with a commercially available vaccine for WNV using an NS1 competition ELISA.

| Horse ID | Day 0[1] | Day 35[2] | % Inhibition |
|---|---|---|---|
| 1 | 1.157 | 0.854 | 26.2 |
| 2 | 1.043 | 0.74 | 29.1 |
| 3 | 0.771 | 0.472 | 38.8 |
| 4 | 1.301 | 0.091 | 93.0 |
| 5 | 1.07 | 0.093 | 91.3 |
| 6 | 0.866 | 1.305 | −50.7 |
| 7 | 1.048 | 0.213 | 79.7 |
| 8 | 1.9 | 0.093 | 95.1 |
| 9 | 0.988 | 0.08 | 91.9 |
| 10 | 0.991 | 0.685 | 30.9 |
| 11 | 1.009 | 0.095 | 90.6 |
| 12 | 0.804 | 0.08 | 90.0 |
| 13 | 0.896 | 0.083 | 90.7 |
| 14 | 1.867 | 0.422 | 77.4 |
| 15 | 0.851 | 0.081 | 90.5 |
| 16 | 1.093 | 0.084 | 92.3 |
| 17 | 0.982 | 0.687 | 30.0 |
| 18 | 1.386 | 0.763 | 44.9 |
| 19 | 1.021 | 0.42 | 58.9 |
| 20 | 1.889 | 0.132 | 93.0 |
| 21 | 1.267 | 0.132 | 89.6 |
| 22 | 1.051 | 0.1 | 90.5 |
| 23 | 1.338 | 0.092 | 93.1 |
| 24 | 1.038 | 0.887 | 14.5 |
| 25 | 0.964 | 0.102 | 89.4 |
| 26 | 1.29 | 0.094 | 92.7 |
| 27 | 0.832 | 0.162 | 80.5 |
| 28 | 0.954 | 0.135 | 85.8 |
| 29 | 1.062 | 0.654 | 38.4 |
| 30 | 0.999 | 0.671 | 32.8 |

[1] Naive horses pre-vaccination with formalin killed WNV vaccine (FDAH)
[2] Two weeks after second vaccination administered on day 21

Example 5

With the development of recombinant viruses that express in vivo in the vaccinated animal only the WNV proteins prM, M and E, the NS1 competition ELISA will be able to differentiate vaccinated horses from those horses infected with WNV. To demonstrate this, blood samples from six control horses and six horses receiving the recombinant vaccine (samples obtained from Merial) were tested in the NS1 competition ELISA prior to vaccination (day 0), three weeks after the first vaccination (day 21), two weeks after the second vaccination on day 35 (day 49), and two weeks after a mosquito challenge with WNV on day 49 (day 63). The competition ELISA was performed as described in Example 3 and the results are shown in Table 5. Only one of the vaccinated horses shows inhibition of greater than thirty percent following vaccination, while 11 of the 12 horses have significant antibodies to NS1 following the mosquito challenge with WNV. This demonstrates the utility of this diagnostic test, when used in combination with the recombinant viral vaccine, to differentiate WNV vaccination from exposure or infection.

TABLE 5

Differentiation of WNV vaccination from WNV viral challenge in the horse using a recombinant virus vaccine and the NS1 competition ELISA

| Horse | | Percent Inhibition | |
|---|---|---|---|
| ID | Treatment | Day 49[a] | Day 63[b] |
| 72 | Control | 7.9 | 85.6 |
| 73 | Control | 11.1 | 85.5 |
| 76 | Control | 22.2 | 72.6 |
| 78 | Control | 29.2 | 85.6 |
| 79 | Control | 27.2 | 91.8 |
| 81 | Control | −6.5 | 47.4 |
| 71 | Vaccinated | 34.6 | 88.7 |
| 75 | Vaccinated | 24.1 | 82.6 |
| 77 | Vaccinated | −10.0 | 88.5 |
| 80 | Vaccinated | 5.8 | 72.7 |
| 83 | Vaccinated | 13.7 | 71.7 |
| 84 | Vaccinated | 12.7 | 4.0 |

[a]Two weeks after second vaccination (day 35)
[b]Two weeks after WNV challenge (day 49)

Example 6

This example demonstrates the ability of a recombinant West Nile Virus envelope protein (rWNV-E) to selectively bind antibodies isolated from horses vaccinated with a recombinant WNV vaccine obtained from Merial recombinant WNV vaccine expressing prM-E antigens as generally described in U.S. Patent Publication No. 2003/0104008.

rWNV-E (L2 Diagnostics, New Haven, Conn.) was incubated in Immulon® 1 microtiter plates (Dynatech Laboratories, Alexandria, Va.) at 1.0 µg/ml in 0.06 M carbonate buffer, pH 9.6, 100 µl/well, overnight at 4° C. Plates were washed with 0.01 M Phosphate buffered saline (PBS, pH 7.4) with 0.05% Tween 20 (PBS/T) (Sigma Chemical Co., St. Louis, Mo.). The plates were blocked with 0.1 M Tris-HCl (pH 8.0) containing 2% casein hydrolysate (Sigma) for 1 hr at 22-25° C. (ambient temperature). Serum samples were obtained from vaccinated and unvaccinated horses at days 0, 21, 35, 49 and 63. The horses were vaccinated first on day 0 and boosted on day 35 (obtained from Merial Ltd). The vaccinated and unvaccinated horse serum samples were diluted 1:100 in IBR gE conjugate diluent (commercially available from IDEXX Laboratories; Product No. 2507523) and added to duplicate wells on the ELISA plates. After 1 hr incubation at ambient temperature, the plates were washed with PBS/T and IgG antibody binding was detected with a peroxidase-conjugated anti-horse IgG antibody (Jackson ImmunoResearch Laboratories Inc., Westgrove, Pa.). After 1 hr incubation, the plates were washed and 100 µl of TMB substrate (available from Moss Inc., Pasadena, Md.). The enzyme reaction was stopped after 5 min at room temperature with 0.1% SDS (Sigma). Optical density (OD) was read versus a PBS blank at 650 nm with an ELISA reader (Vmax® Kinetic Plate Reader, Molecular Devices, Sunnyvale, Calif.). Positive samples were based on an ELISA cut off value of 0.15, determined using serum samples from 8 horses obtained from Alaska (n=8) (Mean+2SD).

As shown in Table 6 below, all vaccinated horses (except horse ID 84V) had detectable levels of IgG antibodies reactive with WNV-E at day 49. Several of the vaccinated horses had IgG antibodies on day 0. Several of the unvaccinated horses also had detectable IgG antibodies to WNV-E at various time points. These results indicate that the horses may have been exposed to WNV or related flavivirus before participating in the vaccine study.

TABLE 6

IgG Response to WNV E-protein

| ID | Day 0[a] | Day 21 | Day 35[b] | Day 49[c] | Day 63[d] | Anti-NS1 (day 63)[e] Inhibition (%) |
|---|---|---|---|---|---|---|
| 72 | 0.09 | 0.09 | 0.11 | 0.13 | 0.70 | 86 |
| 73 | 0.13 | 0.16 | 0.14 | 0.15 | 0.70 | 86 |
| 74 | 0.15 | 0.29 | NA | NA | NA | NA |
| 76 | 0.37 | 0.46 | 0.50 | 0.53 | 1.14 | 73 |
| 78 | 0.34 | 0.56 | 0.50 | 1.33 | 1.10 | 86 |
| 79 | 0.23 | 0.40 | 0.39 | 0.69 | 1.09 | 92 |
| 80 | 0.12 | 0.59 | 0.49 | 1.21 | 1.60 | 73 |
| 81 | 0.06 | 0.10 | 0.10 | 0.28 | 0.78 | 47 |
| 82 | 0.13 | 0.12 | 0.07 | 0.09 | 0.15 | ND |
| 87 | 0.07 | 0.17 | 0.41 | 0.39 | 1.08 | 80 |
| 88 | 0.11 | 0.05 | 0.06 | 0.08 | 0.09 | ND |
| 91 | 0.27 | 0.15 | 0.14 | 1.13 | 0.71 | 80 |
| 71V | 0.21 | 0.56 | 0.53 | 1.01 | 1.23 | 89 |
| 75V | 0.17 | 0.19 | 0.25 | 1.03 | 1.25 | 83 |
| 77V | 0.25 | 0.61 | 0.40 | 0.51 | 1.30 | 89 |
| 83V | 0.13 | 0.53 | 0.38 | 1.17 | 1.11 | 71 |
| 84V | 0.04 | 0.04 | 0.08 | 0.09 | 1.22 | 4 |
| 86V | 0.50 | 0.79 | 0.64 | 0.97 | 1.11 | ND |
| 90V | 0.27 | 0.50 | 0.38 | 0.20 | 1.21 | 92 |

[a] 1st Vaccination;
[b] 2nd Vaccination;
[c] WNV mosquito challenge
[d] 2 weeks post challenge
[e] Inhibition ELISA, see Example 3
V = Vaccinated Sample Although various specific embodiments of the present invention have been described herein, it is to be understood that the invention is not limited to those precise embodiments and that various changes or modifications can be affected therein by one skilled in the art without departing from the scope and spirit of the invention.

What is claimed is:

1. A method for determining whether an animal is infected with West Nile Virus (WNV), or is either not infected or is vaccinated with a WNV subunit vaccine, the method comprising:
   (a) contacting a biological sample from the animal with a first WNV polypeptide that is not an element of the WNV subunit vaccine, wherein the first WNV polypeptide comprises SEQ ID NO:2, and wherein the sample comprises at least one antibody;
   (b) contacting the biological sample with a second WNV polypeptide that is an element of the WNV subunit vaccine; and
   (c) detecting whether the first and the second WNV polypeptides substantially bind to an antibody in the sample,
      wherein if an antibody in the sample substantially binds to the first WNV polypeptide, the animal is naturally infected with WNV, if an antibody in the sample substantially binds to the second WNV polypeptide but not the first WNV polypeptide, the animal has been vaccinated but is not naturally infected, and if an antibody in the sample does not substantially bind to either the first or the second WNV polypeptide, the animal is not vaccinated and not infected.

2. The method of claim 1 wherein the WNV subunit vaccine comprises at least one WNV polypeptide selected from the group consisting of prM, M-E, prM-M-E and B.

3. The method of claim 1 wherein the WNV subunit vaccine comprises a vector encoding at least one polypeptide selected from the group consisting of prM, M-E, prM-M-E and B.

4. The method of claim 1 wherein the second WNV polypeptide is a WNV B, prM, M-B or prM-M-B polypeptide.

5. A method for determining the vaccination or infection status of an animal for WNV comprising:
   (a) contacting a biological sample from the animal with a first reagent comprising a first WNV polypeptide that is not an element of a WNV subunit vaccine, wherein the first WNV polypeptide comprises SEQ ID NO:2, and wherein the sample comprises at least one antibody;
   (b) contacting the biological sample with a second reagent comprising a second WNV polypeptide that is an element of the WNV subunit vaccine; and (c) detecting whether the first and the second WNV polypeptides substantially bind to at least one antibody in the sample,
    wherein if the first WNV polypeptide substantially binds to an antibody in the sample, the animal is infected with WNV, if the first WNV polypeptide does not substantially bind to an antibody in the sample, and the second WNV polypeptide substantially binds to an antibody in the sample, the animal is vaccinated with a vaccine that does not comprise the first WNV polypeptide, and wherein if neither the first nor the second WNV polypeptide substantially binds to an antibody in the sample, the animal is not vaccinated and not infected.

6. The method of claim 5 wherein the WNV subunit vaccine comprises at least one WNV polypeptide selected from the group consisting of prM, M-E, prM-M-E and E.

7. The method of claim 5 wherein the WNV subunit vaccine comprises a vector encoding at least one polypeptide selected from the group consisting of prM, M-E, prM-M-E and B.

8. The method of claim 5 wherein the second WNV polypeptide is a WNV E, prM, M-E or prM-M-E polypeptide.

* * * * *

UNITED STATES PATENT AND TRADEMARK OFFICE
CERTIFICATE OF CORRECTION

PATENT NO. : 7,585,621 B2  Page 1 of 1
APPLICATION NO. : 10/937157
DATED : September 8, 2009
INVENTOR(S) : Beall et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 211 days.

Signed and Sealed this

Fourteenth Day of September, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 388
<212> TYPE: PRT
<213> ORGANISM: West Nile virus
<220> FEATURE:
<221> NAME/KEY: MISC_FEATURE
<223> OTHER INFORMATION: Expression product containing honey bee
      melittin secretory signal sequence upstream of the West Nile virus
      NS1 sequence with 8-His tags.

<400> SEQUENCE: 1

Met Ala Phe Leu Val Asn Val Ala Leu Val Phe Met Val Val Tyr Ile
1               5                   10                  15

Ser Tyr Ile Tyr Ala Ile Met Ala Ile Ser Thr Gly Cys Ala Ile Asn
            20                  25                  30

Ile Ser Arg Gln Glu Leu Arg Cys Gly Ser Gly Val Phe Ile His Asn
        35                  40                  45

Asp Val Glu Ala Trp Met Asp Arg Tyr Lys Tyr Pro Glu Thr Pro
    50                  55                  60

Gln Gly Leu Ala Lys Ile Ile Gln Lys Ala His Lys Glu Gly Val Cys
65                  70                  75                  80

Gly Leu Arg Ser Val Ser Arg Leu Glu His Gln Met Trp Glu Ala Val
                85                  90                  95

Lys Asp Glu Leu Asn Thr Leu Leu Lys Glu Asn Gly Val Asp Leu Ser
            100                 105                 110

Val Val Val Glu Lys Gln Glu Gly Met Tyr Lys Ser Ala Pro Lys Arg
        115                 120                 125

Leu Thr Ala Thr Thr Glu Lys Leu Glu Ile Gly Trp Lys Ala Trp Gly
    130                 135                 140

Lys Ser Ile Leu Phe Ala Pro Glu Leu Ala Asn Asn Thr Phe Val Val
145                 150                 155                 160

Asp Gly Pro Glu Thr Lys Glu Cys Pro Thr Gln Asn Arg Ala Trp Asn

-continued

```
                165                 170                 175
Ser Leu Glu Val Glu Asp Phe Gly Phe Gly Leu Thr Ser Thr Arg Met
            180                 185                 190

Phe Leu Lys Val Arg Glu Ser Asn Thr Thr Glu Cys Asp Ser Lys Ile
            195                 200                 205

Ile Gly Thr Ala Val Lys Asn Asn Leu Ala Ile His Ser Asp Leu Ser
            210                 215                 220

Tyr Trp Ile Glu Ser Arg Leu Asn Asp Thr Trp Lys Leu Glu Arg Ala
225                 230                 235                 240

Val Leu Gly Glu Val Lys Ser Cys Thr Trp Pro Glu Thr His Thr Leu
                245                 250                 255

Trp Gly Asp Gly Ile Leu Glu Ser Asp Leu Ile Ile Pro Val Thr Leu
            260                 265                 270

Ala Gly Pro Arg Ser Asn His Asn Arg Arg Pro Gly Tyr Lys Thr Gln
            275                 280                 285

Asn Gln Gly Pro Trp Asp Glu Gly Arg Val Glu Ile Asp Phe Asp Tyr
            290                 295                 300

Cys Pro Gly Thr Thr Val Thr Leu Ser Glu Ser Cys Gly His Arg Gly
305                 310                 315                 320

Pro Ala Thr Arg Thr Thr Thr Glu Ser Gly Lys Leu Ile Thr Asp Trp
                325                 330                 335

Cys Cys Arg Ser Cys Thr Leu Pro Pro Leu Arg Tyr Gln Thr Asp Ser
            340                 345                 350

Gly Cys Trp Tyr Gly Met Glu Ile Arg Pro Gln Arg His Asp Glu Lys
            355                 360                 365

Thr Leu Val Gln Ser Gln Val Asn Ala Tyr Leu Glu His His His His
            370                 375                 380

His His His His
385

<210> SEQ ID NO 2
<211> LENGTH: 364
<212> TYPE: PRT
<213> ORGANISM: West Nile virus
<220> FEATURE:
<221> NAME/KEY: MISC_FEATURE
<223> OTHER INFORMATION: West Nile virus NS1 sequence with 8-His tags.

<400> SEQUENCE: 2

Ile Ser Thr Gly Cys Ala Ile Asn Ile Ser Arg Gln Glu Leu Arg Cys
1               5                   10                  15

Gly Ser Gly Val Phe Ile His Asn Asp Val Glu Ala Trp Met Asp Arg
            20                  25                  30

Tyr Lys Tyr Tyr Pro Glu Thr Pro Gln Gly Leu Ala Lys Ile Ile Gln
            35                  40                  45

Lys Ala His Lys Glu Gly Val Cys Gly Leu Arg Ser Val Ser Arg Leu
        50                  55                  60

Glu His Gln Met Trp Glu Ala Val Lys Asp Glu Leu Asn Thr Leu Leu
65                  70                  75                  80

Lys Glu Asn Gly Val Asp Leu Ser Val Val Val Glu Lys Gln Glu Gly
                85                  90                  95

Met Tyr Lys Ser Ala Pro Lys Arg Leu Thr Ala Thr Thr Glu Lys Leu
            100                 105                 110

Glu Ile Gly Trp Lys Ala Trp Gly Lys Ser Ile Leu Phe Ala Pro Glu
            115                 120                 125
```

```
Leu Ala Asn Asn Thr Phe Val Val Asp Gly Pro Glu Thr Lys Glu Cys
        130                 135                 140

Pro Thr Gln Asn Arg Ala Trp Asn Ser Leu Glu Val Glu Asp Phe Gly
145                 150                 155                 160

Phe Gly Leu Thr Ser Thr Arg Met Phe Leu Lys Val Arg Glu Ser Asn
                165                 170                 175

Thr Thr Glu Cys Asp Ser Lys Ile Ile Gly Thr Ala Val Lys Asn Asn
            180                 185                 190

Leu Ala Ile His Ser Asp Leu Ser Tyr Trp Ile Glu Ser Arg Leu Asn
        195                 200                 205

Asp Thr Trp Lys Leu Glu Arg Ala Val Leu Gly Glu Val Lys Ser Cys
    210                 215                 220

Thr Trp Pro Glu Thr His Thr Leu Trp Gly Asp Gly Ile Leu Glu Ser
225                 230                 235                 240

Asp Leu Ile Ile Pro Val Thr Leu Ala Gly Pro Arg Ser Asn His Asn
                245                 250                 255

Arg Arg Pro Gly Tyr Lys Thr Gln Asn Gln Gly Pro Trp Asp Glu Gly
            260                 265                 270

Arg Val Glu Ile Asp Phe Asp Tyr Cys Pro Gly Thr Thr Val Thr Leu
        275                 280                 285

Ser Glu Ser Cys Gly His Arg Gly Pro Ala Thr Arg Thr Thr Thr Glu
    290                 295                 300

Ser Gly Lys Leu Ile Thr Asp Trp Cys Cys Arg Ser Cys Thr Leu Pro
305                 310                 315                 320

Pro Leu Arg Tyr Gln Thr Asp Ser Gly Cys Trp Tyr Gly Met Glu Ile
                325                 330                 335

Arg Pro Gln Arg His Asp Glu Lys Thr Leu Val Gln Ser Gln Val Asn
            340                 345                 350

Ala Tyr Leu Glu His His His His His His
        355                 360

<210> SEQ ID NO 3
<211> LENGTH: 377
<212> TYPE: PRT
<213> ORGANISM: West Nile virus
<220> FEATURE:
<221> NAME/KEY: MISC_FEATURE
<223> OTHER INFORMATION: Expression product containing the native
      secretory signal sequence from the 3' end of the West Nile virus E
      protein, NS1 sequence and a V5 tag.

<400> SEQUENCE: 3

Met Asp Arg Ser Ile Ala Leu Thr Phe Leu Ala Val Gly Gly Val Leu
1               5                   10                  15

Leu Phe Leu Ser Val Asn Val His Ala Asp Thr Gly Cys Ala Ile Asp
                20                  25                  30

Ile Ser Arg Gln Glu Leu Arg Cys Gly Ser Gly Val Phe Ile His Asn
            35                  40                  45

Asp Val Glu Ala Trp Met Asp Arg Tyr Lys Tyr Tyr Pro Glu Thr Pro
        50                  55                  60

Gln Gly Leu Ala Lys Ile Ile Gln Lys Ala His Lys Glu Gly Val Cys
65                  70                  75                  80

Gly Leu Arg Ser Val Ser Arg Leu Glu His Gln Met Trp Glu Ala Val
                85                  90                  95

Lys Asp Glu Leu Asn Thr Leu Leu Lys Glu Asn Gly Val Asp Leu Ser
            100                 105                 110
```

```
Val Val Val Glu Lys Gln Glu Gly Met Tyr Lys Ser Ala Pro Lys Arg
            115                 120                 125

Leu Thr Ala Thr Thr Glu Lys Leu Glu Ile Gly Trp Lys Ala Trp Gly
    130                 135                 140

Lys Ser Ile Leu Phe Ala Pro Glu Leu Ala Asn Asn Thr Phe Val Val
145                 150                 155                 160

Asp Gly Pro Glu Thr Lys Glu Cys Pro Thr Gln Asn Arg Ala Trp Asn
                165                 170                 175

Ser Leu Glu Val Glu Asp Phe Gly Phe Gly Leu Thr Ser Thr Arg Met
            180                 185                 190

Phe Leu Lys Val Arg Glu Ser Asn Thr Thr Glu Cys Asp Ser Lys Ile
    195                 200                 205

Ile Gly Thr Ala Val Lys Asn Asn Leu Ala Ile His Ser Asp Leu Ser
210                 215                 220

Tyr Trp Ile Glu Ser Arg Leu Asn Asp Thr Trp Lys Leu Glu Arg Ala
225                 230                 235                 240

Val Leu Gly Glu Val Lys Ser Cys Thr Trp Pro Glu Thr His Thr Leu
            245                 250                 255

Trp Gly Asp Gly Ile Leu Glu Ser Asp Leu Ile Ile Pro Val Thr Leu
                260                 265                 270

Ala Gly Pro Arg Ser Asn His Asn Arg Arg Pro Gly Tyr Lys Thr Gln
    275                 280                 285

Asn Gln Gly Pro Trp Asp Glu Gly Arg Val Glu Ile Asp Phe Asp Tyr
290                 295                 300

Cys Pro Gly Thr Thr Val Thr Leu Ser Glu Ser Cys Gly His Arg Gly
305                 310                 315                 320

Pro Ala Thr Arg Thr Thr Thr Glu Ser Gly Lys Leu Ile Thr Asp Trp
            325                 330                 335

Cys Cys Arg Ser Cys Thr Leu Pro Pro Leu Arg Tyr Gln Thr Asp Ser
                340                 345                 350

Gly Cys Trp Tyr Gly Met Glu Ile Arg Pro Gln Arg His Asp Glu Lys
            355                 360                 365

Thr Leu Val Gln Ser Gln Val Asn Ala
        370                 375

<210> SEQ ID NO 4
<211> LENGTH: 352
<212> TYPE: PRT
<213> ORGANISM: West Nile virus
<220> FEATURE:
<221> NAME/KEY: MISC_FEATURE
<223> OTHER INFORMATION: West Nile virus NS1 sequence with a V5 tag.

<400> SEQUENCE: 4

Asp Thr Gly Cys Ala Ile Asp Ile Ser Arg Gln Glu Leu Arg Cys Gly
1               5                   10                  15

Ser Gly Val Phe Ile His Asn Asp Val Glu Ala Trp Met Asp Arg Tyr
            20                  25                  30

Lys Tyr Tyr Pro Glu Thr Pro Gln Gly Leu Ala Lys Ile Ile Gln Lys
        35                  40                  45

Ala His Lys Glu Gly Val Cys Gly Leu Arg Ser Val Ser Arg Leu Glu
    50                  55                  60

His Gln Met Trp Glu Ala Val Lys Asp Glu Leu Asn Thr Leu Leu Lys
65                  70                  75                  80

Glu Asn Gly Val Asp Leu Ser Val Val Val Lys Gln Glu Gly Met
                85                  90                  95
```

```
                                -continued

Tyr Lys Ser Ala Pro Lys Arg Leu Thr Ala Thr Thr Glu Lys Leu Glu
            100                 105                 110

Ile Gly Trp Lys Ala Trp Gly Lys Ser Ile Leu Phe Ala Pro Glu Leu
            115                 120                 125

Ala Asn Asn Thr Phe Val Val Asp Gly Pro Glu Thr Lys Glu Cys Pro
            130                 135                 140

Thr Gln Asn Arg Ala Trp Asn Ser Leu Glu Val Glu Asp Phe Gly Phe
145                 150                 155                 160

Gly Leu Thr Ser Thr Arg Met Phe Leu Lys Val Arg Glu Ser Asn Thr
                165                 170                 175

Thr Glu Cys Asp Ser Lys Ile Ile Gly Thr Ala Val Lys Asn Asn Leu
            180                 185                 190

Ala Ile His Ser Asp Leu Ser Tyr Trp Ile Glu Ser Arg Leu Asn Asp
            195                 200                 205

Thr Trp Lys Leu Glu Arg Ala Val Leu Gly Glu Val Lys Ser Cys Thr
            210                 215                 220

Trp Pro Glu Thr His Thr Leu Trp Gly Asp Gly Ile Leu Glu Ser Asp
225                 230                 235                 240

Leu Ile Ile Pro Val Thr Leu Ala Gly Pro Arg Ser Asn His Asn Arg
                245                 250                 255

Arg Pro Gly Tyr Lys Thr Gln Asn Gln Gly Pro Trp Asp Glu Gly Arg
                260                 265                 270

Val Glu Ile Asp Phe Asp Tyr Cys Pro Gly Thr Thr Val Thr Leu Ser
            275                 280                 285

Glu Ser Cys Gly His Arg Gly Pro Ala Thr Arg Thr Thr Thr Glu Ser
            290                 295                 300

Gly Lys Leu Ile Thr Asp Trp Cys Cys Arg Ser Cys Thr Leu Pro Pro
305                 310                 315                 320

Leu Arg Tyr Gln Thr Asp Ser Gly Cys Trp Tyr Gly Met Glu Ile Arg
                325                 330                 335

Pro Gln Arg His Asp Glu Lys Thr Leu Val Gln Ser Gln Val Asn Ala
                340                 345                 350
```